United States Patent [19]

Augusto et al.

[11] Patent Number: 4,496,226

[45] Date of Patent: Jan. 29, 1985

[54] ANDED MOTOR CONTROL SYSTEM FOR MOTORIZED OPHTHALMIC INSTRUMENT

[75] Inventors: Peter Augusto, Huntington Beach, Calif.; Donn E. Stevens, Rochester, N.Y.

[73] Assignee: Bausch & Lomb Incorporated, Rochester, N.Y.

[21] Appl. No.: 285,717

[22] Filed: Jul. 22, 1981

[51] Int. Cl.³ ............................................. A61B 3/02
[52] U.S. Cl. .................................... 351/234; 351/235
[58] Field of Search .............................. 351/234, 235; 250/231 SE; 350/6.8

[56] References Cited

U.S. PATENT DOCUMENTS 3,860,330  1/1975  Persson .............................. 351/235
4,240,069 12/1980  Hallein et al. ................. 250/231 SE

OTHER PUBLICATIONS

Clinical Ophthalmology, vol. 1, Chapter 67, "Automated Clinical Refraction" Guyton 1980.

Primary Examiner—John K. Corbin
Assistant Examiner—Paul M. Dzierzynski
Attorney, Agent, or Firm—DeWitt M. Morgan; Howard S. Robbins; Bernard D. Bogdon

[57] ABSTRACT

An improved refractor for use in the subjective examination of human eyes. Each half of the refractor includes a plurality of lens supporting disks, a hub assembly for rotatably supporting the disks, and a comb assembly to space the disks along the optical axis. One of the disks supports at least one set of 4 cross cylinder lenses. Each disk is coupled to a stepping motor for selective rotation. Each motor is, in turn, supported by a bracket which permits rotation equivalent to a partial motor step to insure alignment of the optical elements supported on the disks with the optical axis. The cylinder lenses supported on the disks are also rotated by a stepping motor. The Risley prisms of each half of the refractor are always positioned on the optical axis and rotated by stepping motors. Finally, the refractor includes electronics, including a microprocessor, to control the rotation of the motors as required to move the various optical components as necessary to emulate the ophthalmic prescription of the person whose eyes are being examined.

6 Claims, 9 Drawing Figures

ANDED MOTOR CONTROL SYSTEM FOR MOTORIZED OPHTHALMIC INSTRUMENT

CROSS REFERENCE TO RELATED APPLICATIONS

This application is related to the following cofiled applications: Ser. No. 285,716 of P. Augusto for Motor Control System for Motorized Ophthalmic Instrument; and Ser. No. 285,715 of D. E. Stevens for Motorized Refraction Apparatus.

DESCRIPTION OF THE PRIOR ART

There are a wide variety of refracting instruments used in the clinical practice of ophthalmology and optometry, including: conventional refractors, automated monocular objective refracting devices and automated monocular and binocular subjective refracting devices.

A conventional refractor consists of a pair of housings in which are positioned corrective optics for emulating the ophthalmic prescription required to correct the vision of the patient whose eyes are being examined. Typically, each housing contains sets of spherical and cylindrical lenses mounted in rotatable disks. The two housings are suspended from a stand or wall bracket for positioning in front of the patient's eyes. Further, in front of each refractor housing a number of accessories are mounted, typically on arms, so that they may be swung into place before the patient's eyes. Typically, these accessories include a variable power prism known as a Risley prism, Maddox rods, and a cross cylinder for performing the Jackson cross cylinder test.

In determining a patient's distance prescription, the patient views a variety of alpha numeric characters of different sizes through various combinations of the spherical and/or cylindrical lenses supported in the refractor housings until the correct prescription is emulated. The characters, which are typically positioned 6 meters away, may be on a chart or may be projected on a screen by an acuity projector. For near vision testing the same procedure is repeated, expect that the alpha numeric characters viewed by the patient are positioned on a bracket 20 to 65 centimeters in front of the refractor housing.

The cross cylinder is used to refine the power and axis position of the cylindrical component of the patient's prescription. The cross cylinder is a lens consisting of equal power plus and minus cylinders with their axes 90 degrees apart. It is mounted in a loupe for rotation about a flip axis which is midway between the plus and minus axes. When the cross cylinder is flipped, the plus and minus axes change places.

In the Jackson cross cylinder test, the patient views a target through the spherical and/or cylindrical lenses of the refractor used to emulate the patient's prescription. The cross cylinder is used by lining up its flip axis with the previously determined astigmatism correcting cylinder axis. When the cross cylinder is flipped, if each of its positions produces an equal blur of the target, the astigmatism correcting cylinder axis is proper. If one position is clearer than the other, the astigmatism correcting cylinder axis is rotated toward the cross cylinder axis which makes vision better. The process is continued until an equal blurring is achieved when the cross cylinder is flipped. Then, to check cylinder power, the cross cylinder is rotated 45 degrees, thereby bringing one of its axes parallel with the correcting cylinder axis. The cross cylinder is again flipped, and equal impairment of vision indicates the correct cylinder power. When the astigmatism correcting cylinder is negative and if vision is better with the minus axis of the cross cylinder parallel to the correcting cylinder axis, the cylinder power should be increased, and vice versa. These steps are repeated until equal impairment is observed in each position.

To insure that the flip axis of the cross cylinder is aligned with the previously determined astigmatism correcting cylinder axis and thereafter to maintain the cross cylinder flip axis in coincidence with the cylinder axis through the usual numerous corrections to the cylinder axis, the cross cylinder mechanism is mechanically coupled to the cylinder lenses. U.S. Pat. No. 3,498,699 discloses a cross cylinder loupe assembly mechanically coupled to correcting cylinder lenses in order to maintain proper orientation of the cross cylinder assembly. U.S. Pat. No. 3,860,330 also describes a mechanism for synchronizing the axial orientation of a cross cylinder lens assembly with the cylinder axis of a correcting cylinder lens.

In the above described mechanisms, the cross cylinder is placed in the optical path of the refractor only after the prescription has been initially determined. U.S. Pat. No. 4,185,896 discloses a refractor cross cylinder mechanism in which a pair of cylinder lenses are always in the optical path of each refractor half. Each pair of cylinder lenses has a combined power of zero when their cylinder axes are parallel and a small cross cylinder power when one lens is rotated until its axis is perpendicular to the cylinder axis of the other lens.

A Risley prism is a "rotary prism" used for finding the necessary prismatic correction of a patient's eye. It consists of two ophthalmic prisms of equal power, one in front of the other, and mounted so that the prisms can be rotated about the optical axis of the refractor half. In the initial position the base of one prism corresponds with the edge of the other, so that the two prisms are equivalent to a glass plate with plane parallel faces. The maximum effect is obtained when the bases of the prisms correspond.

As those skilled in the art will appreciate, in order to proceed with the subjective determination of a patient's refractive error, it is necessary to have a starting point. Typically, this is accomplished by an objective examination of a patient's eyes, through various combinations of the spherical and/or cylindrical lenses supported in the refractor housings, with a retinoscope. This procedure, particularly for a previously unrefracted patient, can be quite time consuming. To reduce the time required to make an objective measurement of a patient's refractive power, a number of objective automatic monocular objective refraction devices, also known as automatic infrared optometers, have been developed. Several of these devices are described in and compared with other refracting instruments in *Clincial Ophthalmology*, Volume 1, Chapter 67, "Automated Clinical Refraction", D. L. Guyton, Thomas D. Duane (Editor), Harper & Row, 1980.

A similar instrument developed by Zeiss, and the subject of U.S. Pat. No. 3,791,719, includes a "refractometer attachment" in combination with a motorized refractor. It is stated that the lens disks are rotated by servomotors and that micro switches are used to accurately limit the rotary movement of these motors. In operation, the refractometer attachment delivers signals, corresponding to the state of refraction of the eye, to the servomotors to move one or more of the lenses supported on the lens disks into the optical path to achieve a rough refraction. The apparatus also includes a control unit for manually actuating the servomotors after switching off the automatically operating refractometer. The manually operated control unit is used to move selected corrective lenses in front of the patient's eyes for subjective refraction.

Automated subjective refracting devices include American Optical Corporation's SR III and SR IV subjective refraction systems, Humphrey Instruments' Vision Analyzer, and H. Schwind's Refraktron. The SR III and IV, based on the subjective optometer disclosed in U.S. Pat. No. 3,664,631, uses axially moveable lenses to achieve continuously variable spherocylindric power over a wide range. In operation, the patient looks into the instrument and focuses or aligns a programmed series of special line targets. Like the automatic infrared optometers, these instruments are intended to provide a preliminary refraction that is usually subsequently refined by the practitioner.

The Humphrey Instruments' Vision Analyzer, disclosed in U.S. Pat. No. 3,874,774, is designed to perform the entire binocular refraction, both distance and near, and thus replace the conventional refractor. The instrument includes a projection system in which pairs of variable lenses are incorporated. Light from the targets is collimated, passed through the variable-power lenses, deflected by mirrors designed for interpupillary distance adjustment, and finally collected by a concave viewing mirror located approximately 3 meters away from the patient. The concave mirror reimages the variable-power optics directly in front of the patient's eyes Because the optics are reimaged in front of the patient's eyes, the target appears to be located on the mirror. While intended to replace the conventional refractor, conventional refraction cannot be performed with this instrument. Thus, the starting point for the subjective refraction must be obtained from the patient's prior prescription or an objective refractor. Also, because of the optical design, conventional subjective refraction techniques cannot be used.

The Schwind eye testing instrument includes a refractor having conventional batteries of spherical and cylindrical lenses, an optical system for projecting a series of vision testing slides and a semi-reflective mirror. In operation the patient whose eyes are to be examined is seated in front of the semi-reflective mirror. A blackboard or other similar surface may be placed on the opposite side to provide a non-distracting background. A target image is projected, via a suitable optics, through various combinations of the spherical and/or cylindrical lenses of the refractor halves for viewing by the patient. Though not apparent to the patient, the optical effect is as though the lenses of the refractor were in front of the patient's eyes. As with the Vision Analyzer, conventional objective refraction cannot be performed with the instrument, but must be made with other instrumentation.

In the chapter on Automated Clincial Refraction, D. L. Guyton describes a computer actuated refractor as follows: "Marg et al (24) have taken a more direct approach by developing a computerized system to perform subjective refractions using conventional refractor optics and conventional refracting techniques. The most recent model, Refractor III (FIG. 67-16), is a specially designed binocular refractor containing a full range of trial lenses and accessory optical devices for each eye. The spherical and cylindric lenses, cross cylinders, prisms, Maddox rods, filters, and pinhole apertures are arranged on four disks within each half of the refractor. The disks are driven by stepping motors in response to commands from the computer. The computer instructs the patient by means of tape-recorded of voice-synthesized messages and presents a variety of slides for visual acuity determination and refraction at both distance and near, using random-access slide projectors. The patient responds with a simple push-button box held in his lap as the computer follows a series of flow charts to arrive at the refractive correction and corrected visual acuity."

SUMMARY OF THE INVENTION

An ophthalmic instrument including a base, a rotatable component, a stepping motor for rotating such component, and apparatus including a rotatable support for coupling the component to the shaft of the motor. One of the orientations of the component relative to the base, which position corresponds with a motor detent position, constitutes a reset or zero position. The instrument also includes apparatus for sending signals to the motor to rotate the component and apparatus for interrupting such signals before the magnetic detent position where the component is in its reset position but subsequent to the immediately preceding detent position. The interrupting apparatus includes at least two reflective blocks, a pair of encoders, decoder logic for tranforming analog signals to digital signals and a latch. The decoder logic is coupled between the encoders and the latch; the latch, between the decoder logic and the apparatus for sending signals to the motor. Each of the encoders includes and LED and a phototransistor which sends analog signals to the decoder logic. These signals from each encoder reach a threshold value when the light emitted by the corresponding LED is reflected back by the corresponding one of the reflective blocks. The decoder logic changes the the digital signal sent to the latch when the analog signals from the encoders are both concurrently above their respective threshold value, and the resultant signals ANDed. The latch latches as a function of this change in digital signal and sends a signal to the apparatus for sending signals to the motor to stop sending signals to the motor.

The rotatable component may be an optical element such as a Risley prism, a cylinder lens or a cross cylinder lens. The optical element may be supported in a rotatable mount having gear teeth formed on the periphery thereof and the coupling apparatus may include at least one gear. The gear and mount have different rates of rotation, one being a multiple of the other. With this arrangement, the optical element can be precisely stopped at its reset or zero position without the use of very sensitive and expensive encoders.

DESCRIPTION OF THE PREFERRED EMBODIMENT

Figure 1:
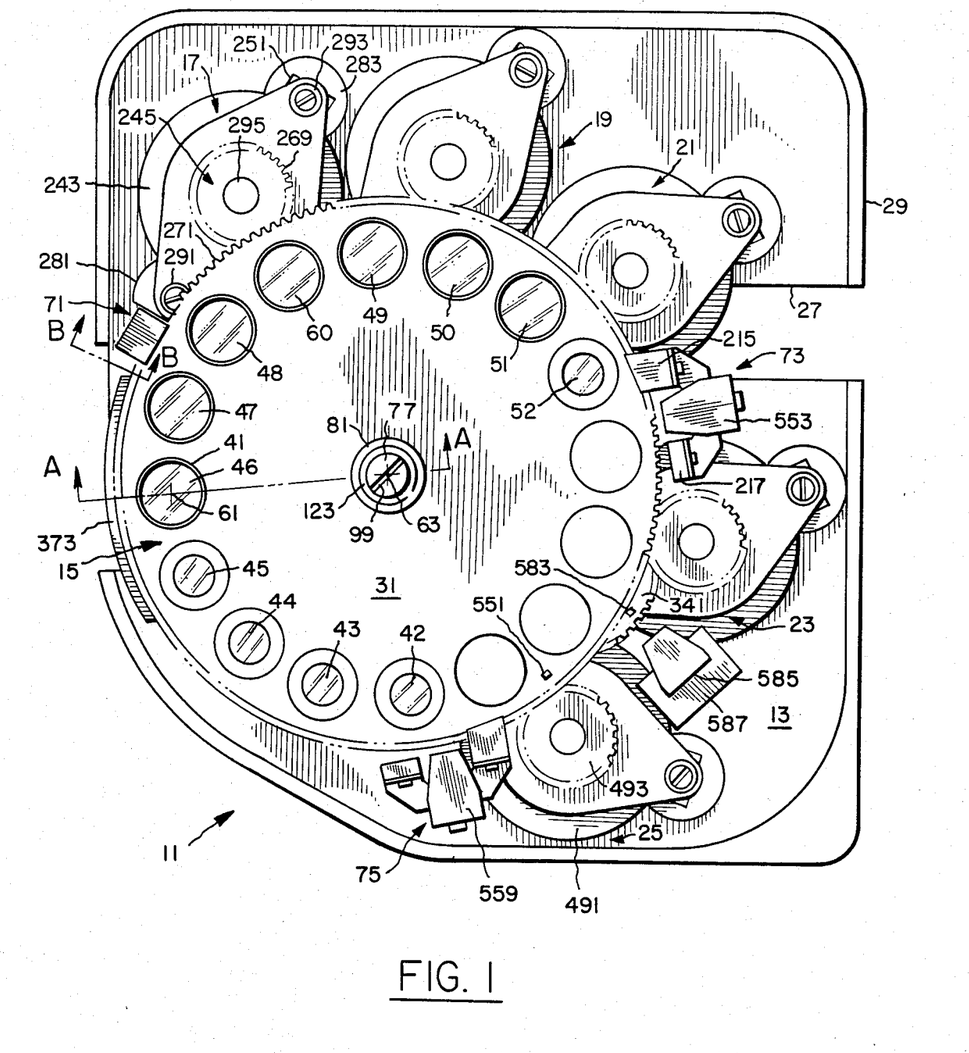
FIG. 1 is a top view of the one of refractor halves of the present invention.

FIG. 1 illustrates, in top plane view, the right refractor half 11 with its cover (not shown) removed. Refractor half 11 is one of two halves of a refractor, such as schematically illustrated in U.S. Pat. No. 4,395,097. Refractor half 11 includes a back plate 13 on which is supported rotatable disk assembly 15 and motor drive assemblies 17, 19, 21, 23 and 25. Back plate 13 includes a cutout 27 through which various wiring harnesses (not shown) pass. Back plate 13 also includes a lip 29 against which the cover seats.

Figure 2:
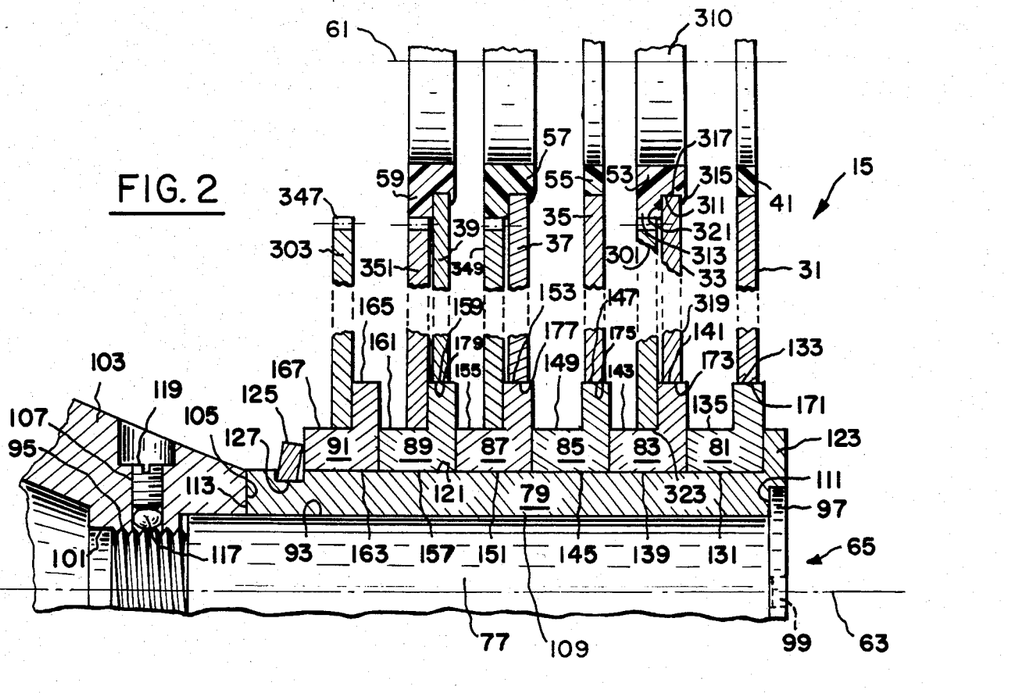
FIG. 2 is an enlarged partial section of the center support for the lens disks taken along Section A—A of FIG. 1.

As best illustrated in FIG. 2, rotatable disk assembly 15 includes five lens supporting disks: strong sphere lens disk 31; strong cylinder lens disk 33; weak sphere lens disk 35; weak cylinder lens disk 37; and auxiliary disk 39. Lens mount 41, disk 31, is one of a series of mounts for supporting the series of strong spherical lenses 42–52, illustrated in FIG. 1. Typically, these lenses range in 4 diopter steps from −28.00 D to +16.00 D. Similarly, rotatable lens mount 53, is one of a series of mounts in strong cylinder lens disk 33 for supporting a series of strong cylinder lenses (not shown). Depending upon the refraction technique to be used, the cylinder lenses will range, typically, in 2 diopter steps from either −2.00 D to −6.00 D or from +2.00 D to +6.00 D. Lens mount 55, in disk 35, is for supporting one of a series of weak spherical lenses (not shown), ranging in ¼ diopter steps from 0.00 D to +3.75 D. Rotatable lens mount 57 is for supporting one of a series of weak cylindrical lenses (not shown). Again, depending on the refraction technique to be used, these lenses will range, typically, in ¼ diopter steps from either −0.25 D to −1.75 D or from +0.25 D to +1.75 D. Finally, rotatable lens mount 59, in auxiliary disk 39, is for supporting the cross cylinder lenses of the present invention as well as a series of well known auxiliary elements (also not shown) such as a pinhole, occluder, filters and Maddox rods. At least one aperture in each of disks 33–39 remains open. In normal operation, a plano lens 60 is in the "open" aperture of disk 31 to provide additional glass thickness to optimize the optical path length when no strong sphere lens is required.

Figure 3:
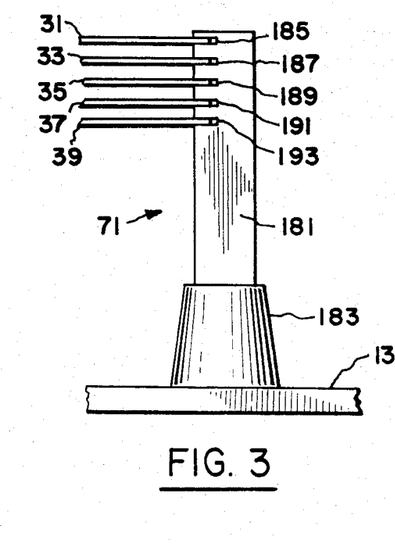
FIG. 3 is a side view of one of the perpherial supports for the lens disks taken along along Section B—B of FIG. 1.
Figure 4:
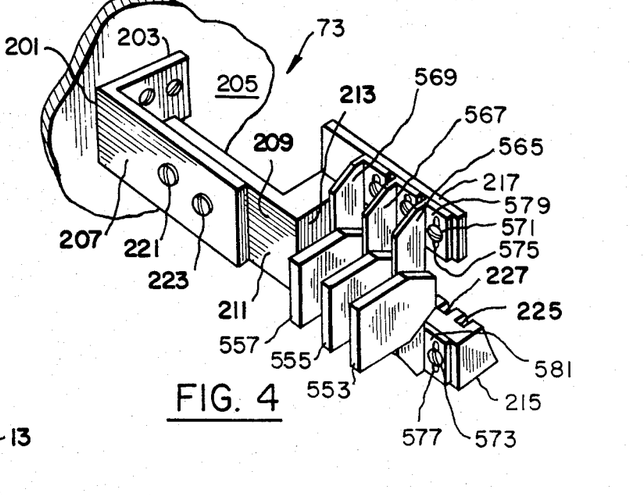
FIG. 4 is a perspective view of another of the peripherial supports for the lens supporting disks.

For the various lenses and auxiliary elements supported on disks 31–39 to be accurately positionable on and along optical axis 61 of refractor half 11, it is necessary that disks 31–39 be accurately positioned relative to rotational axis 63. In the present invention, this is accomplished by radially supporting disks 31–39 with hub assembly 65, as illustrated in FIG. 2. The proper spacing of disks 31–39 along axis 63 is affected by comb assemblies 71, 73 and 75, as shown in FIGS. 1, 3 and 4.

Hub assembly 65 includes a disk shaft 77, a drive tube 79 and spools 81, 83, 85, 87, 89 and 91. Disk shaft 77 includes an elongated cylindrical bearing surface 93, threads 95, a lip 97, and a screw slot 99. Threads 95 are received in the threaded opening 101 provided in boss 103 which is, preferably, formed as an interval part of back plate 13. Boss 103 also includes a surface 105 and a tapped opening 107, as illustrated in FIG. 2. Drive tube 79 includes a bore 109 in which surface 93 of shaft 77 is received. Lip 97 of shaft 77 is received within cutout 111 and shaft 77 is tightened until rear surface 113 of drive tube 79 engages surface 105 of boss 103, and then backed off to allow drive tube 79 to rotate about shaft 77. A soft plastic ball 117 received within tapped opening 107 is forced against threads 95 by a set screw 119 to prevent further rotation of disk shaft 77.

Supported on surface 121 of drive tube 79 and captured between lip 123 and bowed lock ring 125, received in groove 127, are spools 81–91. Spool 81 includes an internal cylindrical bore 131, which snuggly fits over surface 121, cylindrical bearing surface 133 and surface 135. Identically, spool 83 includes bore 139 and surfaces 141 and 143; spool 85, bore 145 and surfaces 147 and 149; spool 87, bore 151 and surfaces 153 and 155; spool 89, bore 157 and surfaces 159 and 161; and spool 91, bore 163 and surfaces 165 and 167. Spools 81–91 are keyed to drive tube 79 so as to prevent relative rotation.

As is also evident from inspection of FIG. 2, each of disks 31–39 includes, respectively, bearing apertures 171, 173, 175, 177 and 179. To radially align disks 31–39 relative to axis 63, disk 31 is fitted over surface 133; disk 33, over surface 141; disk 35, over surface 147; disk 37, over surface 153; and disk 39, over surface 159.

The positioning of disks 31, 33, 35, 37 and 39 along axis 61 is accomplished by comb assemblies 71, 73 and 75, illustrated in FIGS. 1, 3 and 4. With reference to FIG. 3, comb assembly 71 comprises an upright post 181 secured to boss 183 of back plate 13 by, preferably, a bolt (not shown). Post 181 is provided with five grooves 185, 187, 189, 191 and 193 which are spaced relative to each other so as to hold lens disks 31–39 at those intervals along optical axis 61 which will result in the required optical element air spacing between the lenses supported on lens disks 31–39. Each of grooves 185–193 is dimensioned so as to provide a bearing fit for its respective disk. Since, in the preferred embodiment disks 31–39 are stamped out of 0.050 inch thick sheet metal and are ordinarily flat within 0.005 inches, post 181 is positioned adjacent optical axis 61 to insure that the required optical air spacing is maintained along axis 61.

As illustrated in FIG. 4, comb assembly 73 includes an L-shaped support bracket 201, the short leg 203 of which is secured, via bolts (not shown), to boss 205 provided on back plate 13. Secured to upstanding leg 207 is fork member 209 which includes a base portion 211, an offset portion 213, and a pair of fork members 215 and 217. Base portion 211 is secured to leg 207 via screws 221 and 223 which pass through enlarged holes (not shown) in legs 207 and 211 and are received in a Tinnerman type nut plate (also not shown). The enlarged holes permit both height and angular adjustment. Fork member 215, like post 181 of comb assembly 71, is provided with five equally spaced grooves, of which 225 and 227 are illustrated in FIG. 4. These grooves, also dimensioned so as to provide a bearing fit, in association with grooves 185–193 of comb assembly 71 and an identical set of grooves (not shown) provided on comb assembly 75, position disks 31–39 along optical axis 61. Fork member 217 includes no grooves.

Figure 5:
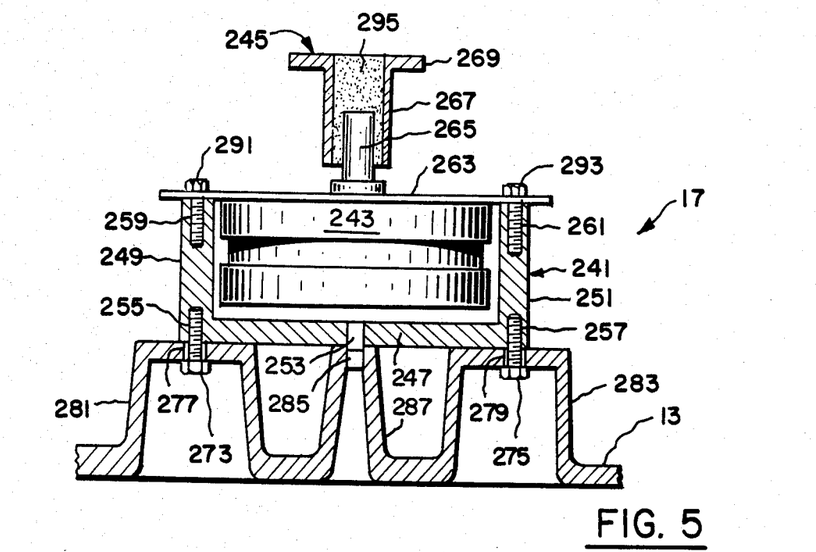
FIG. 5 is a partial sectional view of one of the lens disk drive motors and its associated support.

In order to selectively rotate disks 31–39 about axis 63, to align one or more lenses and/or auxiliary elements with optical axis 61, as required to emulate a patient's ophthalmic prescription, disks 31-39 are coupled to, respectively, motor drive assemblies 17-25. With reference to FIGS. 1 and 5, assembly 17 includes motor support bracket 241, stepping motor 243 and pinion 245. Bracket 241 includes a base 247 and two upstanding legs 249 and 251. Base 247 includes a pin 253 and tapped holes 255 and 257. Legs 249 and 251 include, respectively, tapped holes 259 and 261. Motor 243, preferably North American Phillips K82701-P2 or equivalent, includes an integral frame bracket 263 and a drive shaft 265. Pinion 245 includes a hollow hub 267 and gear teeth 269 which mesh with teeth 271 formed on the periphery of disk 31. In the preferred embodiment, the gear ratio between pinion 245 and disk 31 is chosen such that for every 18 steps of motor 243, disk 31 is rotated from a position where one lens is aligned with axis 61 to a position where an immediately adjacent lens or opening is aligned with axis 61.

As assemblied, bracket 241 is secured to back plate 13 via screws 273 and 275 which pass through washers (not shown) and enlarged openings 277 and 279 in bosses 281 and 283 formed in back plate 13. Pin 253 is rotatably received in opening 285 of boss 287, which is also integral with back plate 13. Enlarged openings 277 and 279 permit the position of bracket 241 to be angularly adjusted about the axis of pin 253. Motor frame bracket 263 is secured to bracket 241 via motor attachment screws 291 and 293 which pass through washers and enlarged openings therein (not shown). Pinion 245 is secured to drive shaft by means of an elastomeric material 295 bonded to both members.

To remove the backlash between teeth 269 and teeth 271 and to reduce noise, pinion 245 is "spring loaded" into engagement with disk 31. With motor attachment screws 291 and 293 loosened, motor frame bracket 263 is moved toward axis 63 until all backlash is removed from the gear mesh. Motor frame bracket 263 is then moved an additional incremental distance toward axis 63 and screws 291 and 293 tightened to thereby clamp motor frame bracket 263 to bracket 241. This second predetermined movement displaces elastic material 295 to, in effect, "spring load" gear teeth 269 of pinion 245 into engagement with gear teeth 271 on disk 31.

Since the stepping motors are programmed to index only in integral steps, the optical axes of the strong sphere lenses supported on lens disk 31 may, within the rotational increment of disk 31 produced by one step of motor 243, be offset from optical axis 61. To insure optical alignment, it is necessary to provide for limited rotation of motor frame bracket 263. This angular rotation is permitted by the coupling between motor support bracket 241 and back plate 13. With bracket attachment screws 273 and 275 loosened, motor 243 is energized to hold it in one of its magnetic detent positions. Motor 243 and bracket 241 are then rotated about the axis of pin 253 until the required optical alignment is achieved. In the preferred embodiment this is determined with a test fixture (not shown) referenced to an open aperture in disk 31. Since the gear ratio between pinion 245 and disk 31 is chosen so that for every 18 steps of motor 243 disk 31 is rotated from a position where one lens or opening is aligned with axis 61 to a position where the immediately adjacent lens or opening is aligned with axis 61, alignment of an open aperture in disk 31 with optical axis 61 insures alignment of the optical axes of all the strong sphere lenses with axis 61. Once aligned, bracket attachment screws 273 and 275 are tightened. The gear mesh between teeth 269 and 271 is effectively unchanged since the displacement between the axis of drive shaft 265 and the axis of pin 253 is minimal.

With the exception of the height of the bosses on which they are mounted, motor drive assemblies 19-25 are identical to motor drive assembly 17. Further, the structure and method of removing backlash and noise, and achieving optical alignment for the lenses and optical elements supported on disks 33-39 is the same as that used for disk 31.

Figure 6:
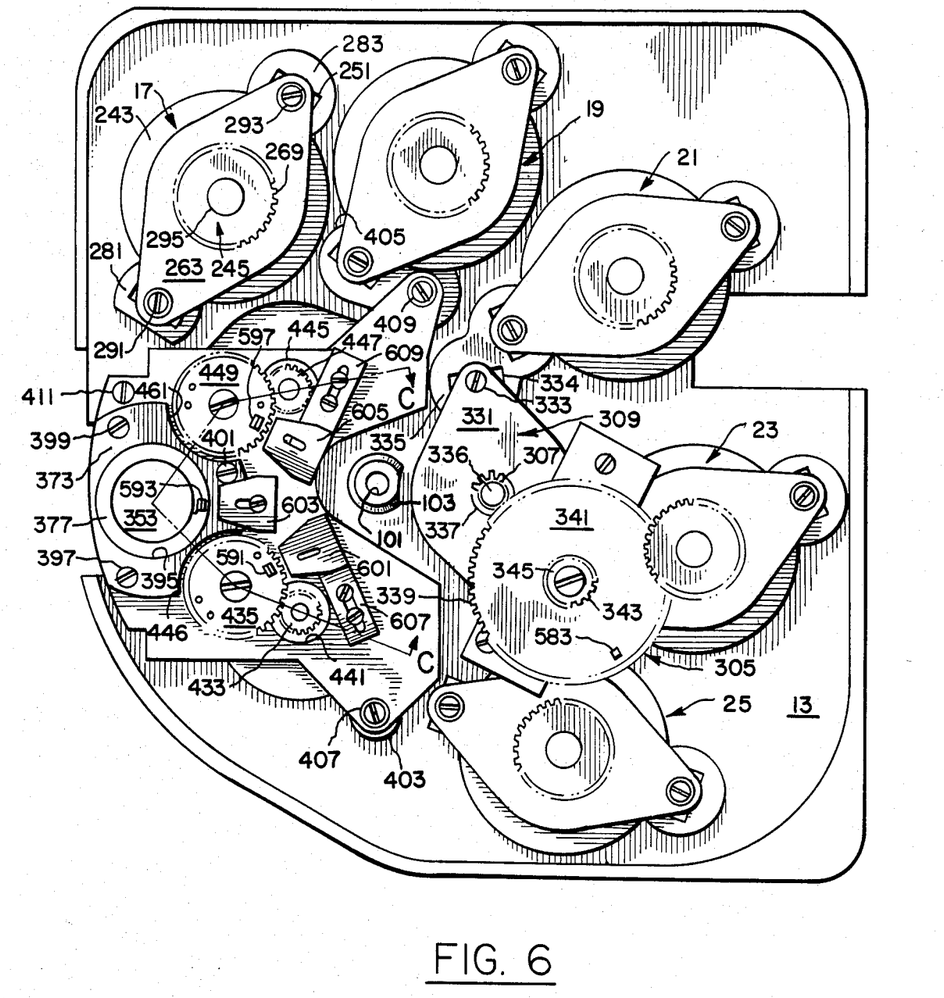
FIG. 6 is a top view of the refractor half of FIG. 1 with the lens disks removed.

As those skilled in the art will appreciate, the axes of the cylinder lenses supported on disks 33 and 37 must be rotatable about axis 61 in order to orientate the cylinder axes so as to neutralize a patient's cylinder refractive error. The axes of the cross cylinder lenses supported on auxiliary disk 39 must also be rotatable about axis 61 and this rotation synchronized with the rotation of the cylinder lenses. The structure for producing these required rotations is illustrated in FIGS. 2 and 6. With reference to disk 33, this structure includes a plurality of rotatable lens mounts, such as mount 53, bull gear 301, spool 83, drive tube 79, spool 91, cylinder axis drive gear 303, gear cluster 305, pinion 307 and stepping motor 309.

Lens mount 53 includes aperture 310 having a lens supporting seat (not shown), bearing surface 311, shoulder 313, gear teeth (not shown) and three evenly spaced tabs, one of which is illustrated at 315. As assembled, surface 311 bears against the surface of cylindrical opening 317 of disk 33, with tab 315 hooking disk face 319 to thereby hold shoulder 313 against disk face 321. Bull gear 301 includes teeth (not shown), which mesh with the gear teeth (also not shown) on lens mount 53, and a cylindrical aperture 323 in which is received surface 143 of spool 83. Aperture 323 includes a key slot (not shown) which cooperates with a key (also not shown) provided on spool 83 to prevent relative rotation therebetween. To prevent relative movement along axis 63, bull gear 301 is cemented to spool 83.

Stepping motor 309, preferably a North American Phillips K82401-P2 or equivalent, includes an integral frame bracket 331 which is secured via screws, such as illustrated at 333, to motor support bracket 334 which, in turn, is secured to bosses, such as illustrated at 335 provided on back plate 13. Pinion 307, rigidly coupled to motor shaft 336, includes teeth 337 which mesh with teeth 339 on gear 341 of gear cluster 305. Teeth 343 of pinion 345 mesh with teeth 347 of axis drive gear 303. As axis drive gear 303 is both keyed and cemented to spool 91 and as spools 91 and 83 are both keyed to drive tube 79, rotation of stepping motor 309 rotates bull gear 301 which, in turn, rotates lens mount 53 and the cylinder lens (not shown) supported therein.

The rotatable lens mounts, such as illustrated at 57 and 59 of FIG. 2, provided on disks 37 and 39 are coupled to drive tube 79 via, respectively, bull gears 349 and 351, which are keyed and cemented to, respectively, spools 87 and 89. With this arrangement, rotation of motor 309 produces simultaneous rotation of lens mounts 53, 57 and 59.

As those skilled in the art will appreciate, in addition to being simultaneously rotatable, the cylinder and cross cylinder lenses supported on disks 33, 37 and 39 must be prealigned and synchronized. Synchronization is accomplished by the gearing. All the lens mounts, as exemplified by mounts 53, 57 and 59, have the same number of gear teeth. Further, each of bull gears 301, 349 and 351 have the same number of gear teeth. With reference to disk 33, the number of teeth on lens mount 53 and bull gear 301 is chosen such that each complete rotation of bull gear 301, about axis 63 relative to disk 33, produces a multiple of 180 degree rotations of lens mount 53. In the preferred embodiment, bull gear 301 is provided with 195 teeth and lens mount 53 with 39 teeth. With this arrangement, every complete rotation of bull gear 301 produces 5 complete rotations of lens mount 53.

With reference to strong cylinder lens disk 33, the first step in the alignment procedure is to assemble and cement bull gear 301 to spool 83. With all the necessary rotatable lens mounts, such as mount 53, assembled thereto, disk 33 is assembled to spool 83. Next, the alignment mark (not shown) provided on, for instance, mount 53 is aligned with the alignment mark (also not shown) provided on bull gear 301. This latter mark is aligned with the key slot provided in bull gear 301 to define an axis which is perpendicular to axis 63. This procedure is repeated for all the lens mounts on disk 33. With the aid of a fixture, which includes a source of collimated light, the required cylinder lens is inserted in mount 53, such that the cylinder axis is perpendicular to axis 63, and then cemented in place. This process is repeated for the remaining strong cylinder lenses.

With the weak cylinder lenses assembled to disk 37 and the cross cylinder assembled to disk 39 utilizing the procedure as set forth above, spools 83, 87 and 89 and the structure supported thereon are, together with spools 81, 85 and 91 and the structure supported thereon, assembled on drive tube 79, as illustrated in FIG. 2.

Since stepping motor 309 is programmed to index only in integral steps, the axes of the cylinder lenses supported on disks 33 and 37 may, within the rotation increment of the lens mounts produced by one step of motor 309, not be correct. To insure proper angular orientation, it is necessary to provide for limited rotation of motor frame bracket 331, via motor support bracket 334 which attaches to back plate 13 and functions in the same manner as motor support bracket 241.

In contrast to prior art refractors in which each Risley prism mechanism is movable into and out of the optical axis, in the present invention Risley prisms 353 and 355 are always positioned along axis 61. Accordingly, when not in use they must be orientated relative to each other so that they are essentially equivalent to a glass plate with parallel faces. Prisms 353 and 355 and the supporting and rotating mechanisms, illustrated in FIGS. 6 and 7, includes support assembly 357, motor assemblies 359 and 361 and gear trains 363 and 365.

Figure 7:
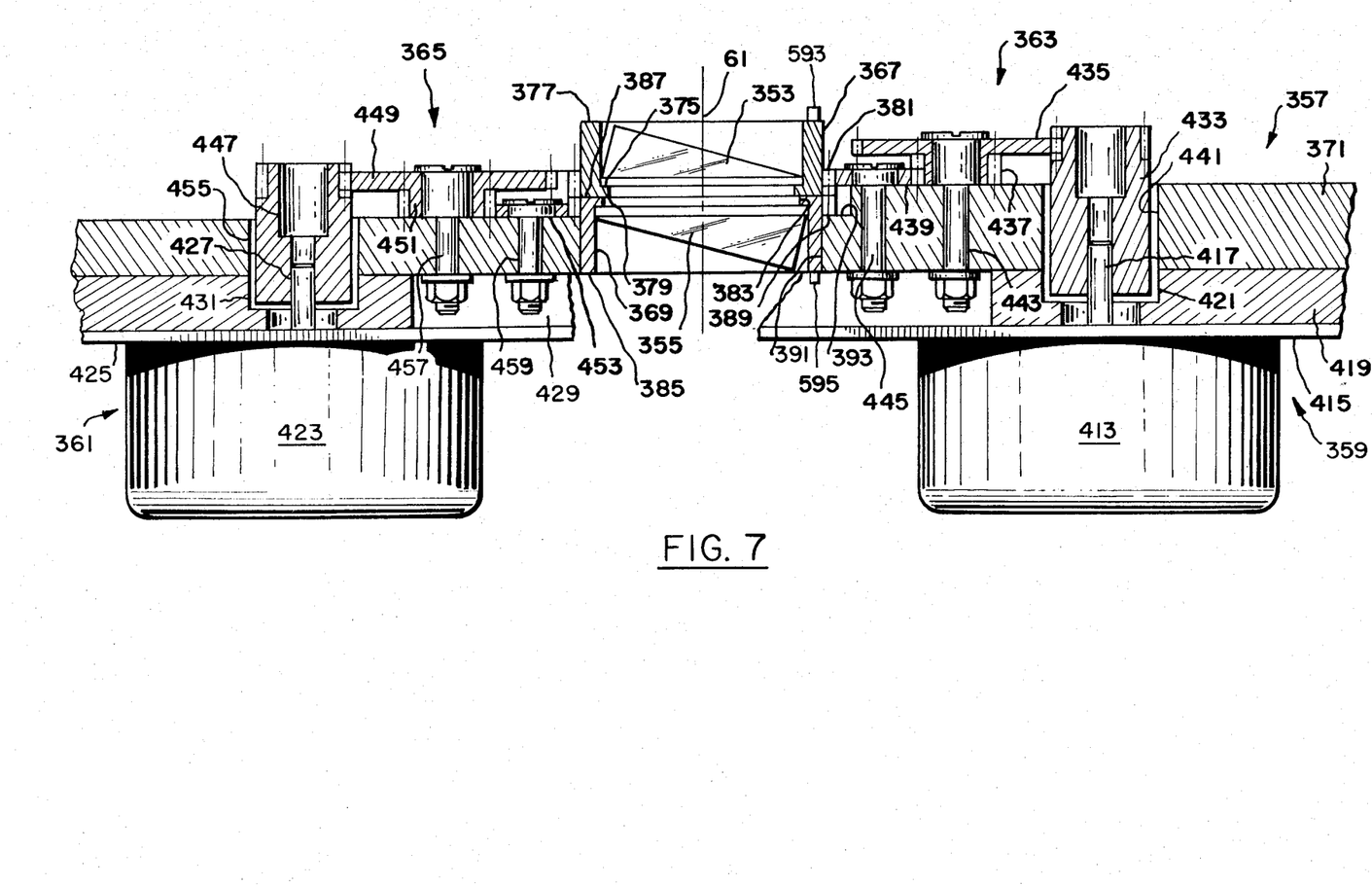
FIG. 7 is a partial sectional view of the Risley prism mechanism taken along Section C—C of FIG. 6.

Support assembly 357 includes prism mounts 367 and 369, base plate 371 and cover plate 373. As illustrated in FIGS. 6 and 7, prism mount 367 is essentially a hollow cylindrical member having a lip 375 against which prism 353 is seated. Prism mount 367 also includes faces 377 and 379 and a shoulder 381 on which are provided gear teeth (not shown). Similarly, prism mount 369 includes lip 383, faces 385 and 387 and shoulder 389 having gear teeth thereon (also not shown). Prism mount 369 is received within opening 391 provided in base plate 371 with shoulder 389 seating against shoulder 393. Prism mount 367 is received within opening 395 of and held in place by cover plate 373. Internal shoulders provided on cover plate 373 (not shown) position and hold face 379 in bearing engagement with face 387. Cover plate 373 is secured to base plate 371 by screws 397, 399 and 401. In turn, base plate 371 is secured to bosses, such as illustrated at 403 and 405, provided on back plate 13, via screws 407, 409 and 411.

Motor assembly 359 includes stepping motor 413, integral frame bracket 415, drive shaft 417 and an alignment plate 419, which includes stepped opening 421. In the preferred embodiment, motor 413 is a North American Phillips K82401-P2 or equivalent. Bracket 415 is secured to plate 419 via clips (not shown), while plate 419 is secured to base plate 371 via screws (not shown) which pass through enlarged openings therein (also not shown). In a like manner, motor assembly 361 includes stepping motor 423, integral frame bracket 425, drive shaft 427 and alignment bracket 429 having stepped opening 431.

Gear train 363 includes pinion 433, integrally formed gears 435 and 437 and gear 439. Pinion 433, secured to drive shaft 417, is received within stepped opening 421 and opening 441 provided in base plate 371, as illustrated in FIG. 7. Gears 435 and 437 are secured to plate 371 via an eccentric shoulder bolt 443. Gear 439, which is mounted on eccentric shoulder bolt 445, engages the gear teeth (not shown) provided on shoulder 381 of prism mount 367. As is evident from inspection of FIG. 6, the teeth on shoulder 381 are exposed via cutout 446 in cover plate 373. Similarly, gear train 365 includes pinion 447, integrally formed gears 449 and 451 and gear 453. Pinion 447, secured to drive shaft 427, is received within opening 455 provided in base plate 371 and stepped opening 431. Gears 449 and 451 are secured to plate 371 via eccentric shoulder bolt 457; gear 453, via eccentric shoulder bolt 459. The teeth (not shown) provided on shoulder 389 of prism mount 369 are exposed by cutout 461.

In the preferred embodiment, prism mount 367 is provided with 63 gear teeth, gear 439 with 20 teeth, gear 437 with 21 teeth, gear 435 with 50 teeth and pinion 433 with 20 teeth. This results in a motor pinion to prism mount gear reduction of 7.5 to 1. Thus, a single step of stepping motor 413, which produces a pinion rotation of 7.5 degrees, results in a one degree rotation of prism mount 367. The gear reduction between pinion 447 and prism mount 369 is also 7.5 to 1 so that each step of motor 423 produces a one degree rotation of prism mount 369. In assembly, the backlash between gear 439 and prism mount 367 is adjusted by rotation of eccentric shoulder bolt 445. Similarly, the backlash between gear 439 and 437 is adjusted by rotation of shoulder bolt 443. With motor frame bracket 415 clamped to adjusting plate 419 via clips (not shown), the screws (not shown) which hold adjusting plate 419 to base plate 371 are loosened and adjusting plate 419 is moved toward the axis of gear 435 until the desired gear backlash adjustment between gear 435 and pinion 433 is obtained. The screws clamping adjusting plate 419 to base plate 371 are then tightened. The same process, utilizing adjustment plate 429, is used to adjust the gear backlash between pinion 447 and gear 449.

To orient prisms 353 and 355 so that when not in use they effectively optically neutralize each other, it is necessary to step motors 413 and 423 until the optical bases of prisms 353 and 355 are 180 degrees apart. Since motors 413 and 423 are programmed to index only in integral steps, it may not be possible to orient prisms 353 and 355 accurately enough to neutralize each other completely without rotating at least one of motor frame brackets 415 and 425 to simulate a partial motor step. This is accomplished by energizing motor 413 to utilize its magnetic detent effect, unclamping the clips (not shown) which clamp motor frame bracket 415 to adjusting plate 419 and then rotating bracket 415 until the desired optical relationship is obtained between prisms 353 and 355. As motor shaft 417 is piloted in recess 421 of the adjusting plate 419, rotation of bracket 415 will not change the motor shaft center line location which, in turn, keeps the gear system backlash from changing. Alternately, this orientation of prisms 353 and 355 can be accomplished by rotation of motor frame bracket 425 relative to adjusting plate 429.

Once the prisms 353 and 355 have been relatively located so as to completely neutralize each other, it is necessary to set the prism base direction accurately. First, prisms 353 and 355 are each counter-rotated 90 degrees so as to bring their bases into an alignment which will result in the maximum additive prism power. The two prisms are then rotated together, by use of stepping motors 413 and 423, until the base direction of the prism pair is, for example, in the "base out" orientation. This measurement can be made with any of several appropriate optical methods, such as projecting a laser beam through prisms 353 and 355 and observing the direction of the deflection. If the exact "base out" direction cannot be obtained by identical integral steps of the motors 413 and 423, it will be necessary, with the motors energized, to rotate both motor frame brackets 415 and 425 in unison, utilizing the same procedure used to initially orientate prisms 353 and 355. The motor frame brackets 415 and 425 are then reclamped.

With the foregoing arrangement, Risley prisms 353 and 355 are controlled so that the full prism power range, in 0.50 D steps, in the base out, base in, base up or base down, configuration can be effectively introduced in optical path 61.

In contrast to prior art where the Jackson cross cylinder test is performed by flipping the cross cylinder about the flip axis, in the present invention the test is performed by utilizing one of two sets of 4 cross cylinders mounted on auxiliary disk 39. Each cross cylinder is mounted in a rotatable lens mount, such as illustrated at 59 in FIG. 2. As such mounts have the same number of gear teeth as mounts 53 and 57, as bull gear 351 is identical to bull gears 301 and 349, and because bull gears 301, 349 and 351 are keyed to drive tube 79, rotation of the cross cylinders is synchronized with rotation of the cylinder lenses. Further, the cross cylinder lenses are prealigned, with the same technique utilized for aligning the cylinder lenses.

Figure 8:
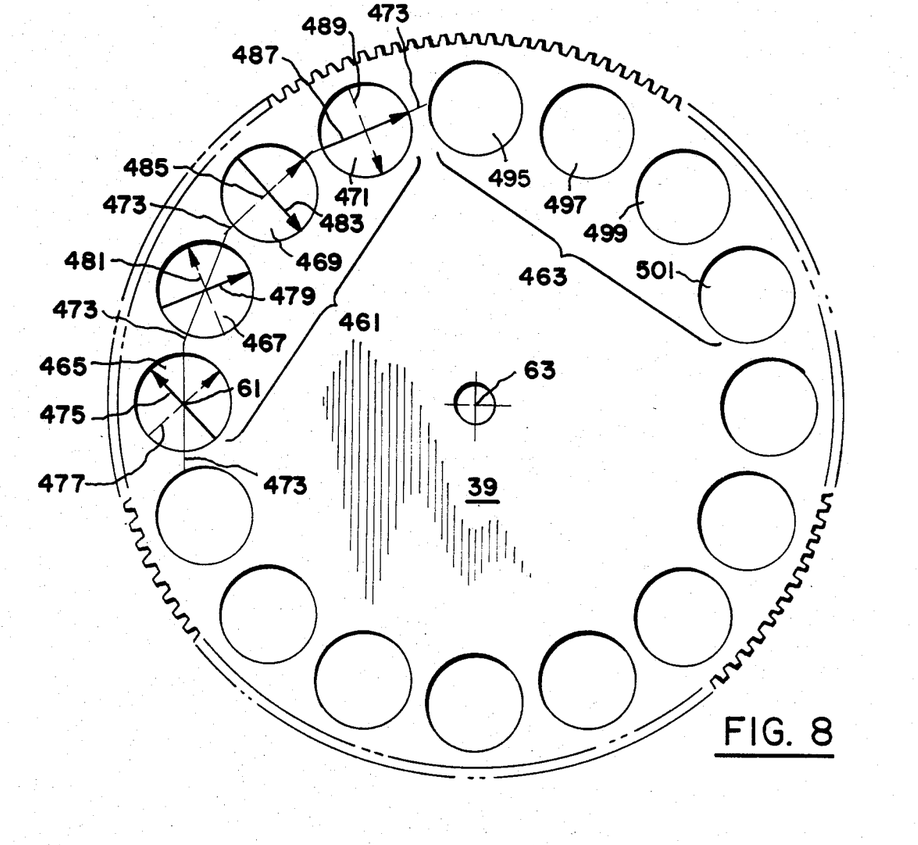
FIG. 8 is a schematic view of the auxiliary disk showing how the cross cylinders are mounted thereon.

With reference to FIG. 8, auxiliary disk 39 includes set 461 of 0.50 D cross cylinders and a set 463 of 0.25 D cross cylinder lenses. Set 461 includes cross cylinder lenses 465, 467, 469 and 471. The orientation of the axes of the cylinder lens or lenses used to neutralize a patient's cylinder refractive error is represented by axis 473. As those skilled in the art will appreciate, the illustrated orientation of axis 473 relative to lens 465 and optical axis 61 is arbitrary. As those skilled in the art will also appreciate, the illustrated orientation of axis 473 relative to lenses 467-471 is for convenience of explanation only. Because lenses 467-471 are supported in rotatable mounts, which rotate relative to disk 39 as disk 39 is rotated about axis 63, the correct orientation is determined by the gear ratio between these rotatable lens mounts and bull gear 351. For refining axis, 475 represents the direction of the positive cylinder axis of lens 465. It is orientated at 135 degrees relative to axis 473. Similarly, 477 represents the direction of the negative cylinder axis, orientated at 45 degrees relative to axis 473. With regard to lens 467, 479 represents the direction of the positive cylinder axis; 481, the direction of the negative cylinder axis. Relative to axis 473, axis 479 is orientated at 45 degrees; axis 481, at 135 degrees. For refining power, lenses 469 and 471 are utilized. In this case 483, which represents the direction of the positive cylinder axis of lens 469, is perpendicular to axis 473; 485, the negative cylinder axis, is parallel to axis 473. For lens 471 the positive cylinder axis is 487; the negative, 489.

In operation, to refine cylinder axis, auxiliary disk 39 is rotated until lens 465 is aligned with optical axis 61. As they are prealigned and synchronized with the cylinder lenses, axis 475 is orientated at 135 degrees and axis 477 at 45 degrees relative to the axis of the cylinder lens or lenses which neutralize the patient's cylinder refractive error. To refine axis, stepping motor 491 of motor drive assembly 25 is energized to rapidly rotate disk 39, via pinion 493, from the position where lens 465 is aligned with axis 61 to the position where lens 467 is in alignment with axis 61. If each of lenses 465 and 467 produces an equal blur of the target being viewed, the orientation of the axis of the cylinder lens or lenses is proper. If one position is clearer than the other, the axis of the correcting cylinder lens or lenses is rotated toward, when the cylinder lens or lenses are positive, the one of cross cylinder axes 475 and 479 which produced better vision. Disk 39 is then again rotated to align the other of lenses 465 and 467 with axis 61 to again determine if both lenses 465 and 467 produce an equal blur. If not, the process is repeated until equal blurring is achieved.

To refine cylinder power, lenses 469 and 471 are utilized. As is evident from inspection of FIG. 8, negative cylinder axis 485 is parallel to the orientation of the axis of the cylinder lens or lenses which neutralize the patient's refractive error, while negative cylinder axis 489 is perpendicular thereto. If each of lenses 469 and 471 produces equal blurring, the power is correct. When the correcting cylinder is negative and if vision is better with lens 469, when the minus axis 485 is parallel to the correcting cylinder axis, the power should be increased and vice versa. This procedure is repeated until equal impairment of vision is obtained with both lenses 469 and 471.

Lens set 463 includes lenses 495, 497, 499 and 501. Expect for the fact that they are all of 0.25 D power, they are identical in function and orientation with lenses 465-471. Thus, lenses 495 and 497 have their axes orientated for refining cylinder axes, and lens 499 and 501 have their axes orientated for refining power.

Figure 9:
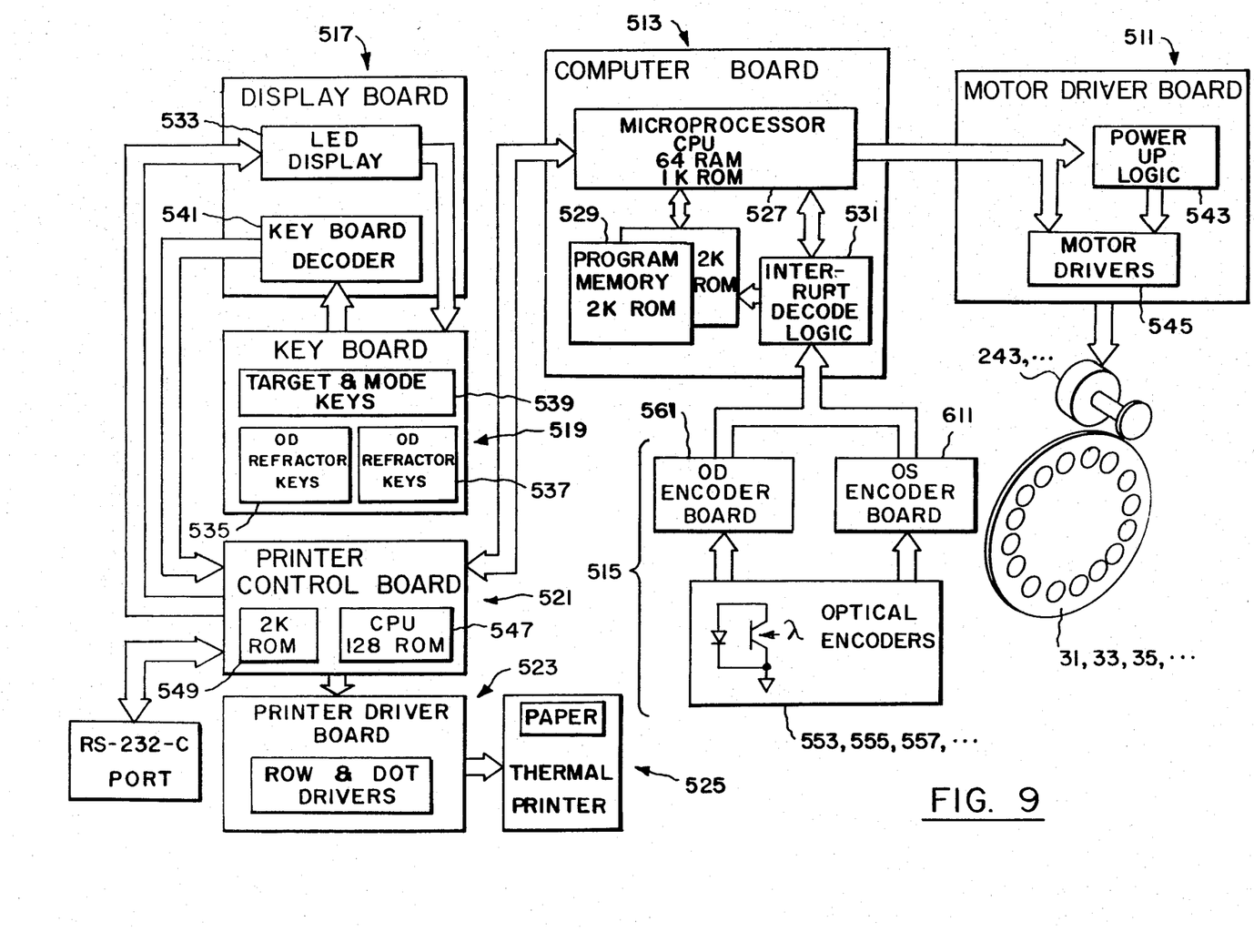
FIG. 9 is a block diagram of the control, drive and display electronics of the present invention.

Each of disks 31-39 is driven by, respectively, the stepping motors of motor drive assemblies 17-25. Similarly, stepping motor 309 drives the rotatable lens mounts exemplified by mounts 53, 57 and 59 illustrated in FIG. 2, and stepping motors 413 and 423 rotate Risley prisms 353 and 355. In total, each refractor half includes 8 stepping motors, each of which must be driven by electrical pulses to incrementially rotate disks 31-39, the rotatable lens mounts and Risley prisms 353 and 355, as necessary to emulate the ophthalmic prescription required to correct the vision of the patient whose eyes are being examined. With reference to FIG. 9, these pulses are supplied by motor driver board 511 which, in turn, is controlled by computer board 513. The electronics also includes an encoder system 515, a display board 517, a key board 519, a printer control board 521, a printer driver board 523 and a thermal printer 525.

The heart of the electronics is computer board 513 which includes microprocessor chip 527, read only memory chips 529 and interrupt decoder logic system 531. In the preferred embodiment, microprocessor 527 is an Intel 8048 or 8748 or equivalent, and memory chips 529 are Intel 8355 or 8755 or equivalent. As is evident from inspection of FIG. 9, microprocessor 527 sends information to LED display 533 of display board 517, via printer control board 521. If the refractor is in the reset mode, wherein all of disks 31–39, lenses and Risley prisms 353 and 355 are in their reset or zero position, display 533 will indicate this. Further, as disks 31–39 and the other optical components are rotated, microprocessor 527 sends information to display 533 to tell the instrument operator which optical elements are positioned along optical axis 61 and, where appropriate, their orientation. Microprocessor 527 also periodically checks to see if new instructions are coming from key board 519.

Key board 519 includes a set of OD refractor keys 535 and a set of OS refractor keys 537. In the preferred embodiment, the keys are dome or membrane switches. Set 535 includes plus and minus directional keys for each of the motors which drive disks 31–37, motor 309, and motors 413 and 423. In operation, when one of these keys is depressed, the associated motor is energized for the number of steps required to move the associated optical element from one operational position to the adjacent operational position. In addition, the directional keys for motors 309, 413 and 423 are coupled to a high speed interlock key which, when depressed, provides for high speed rotation. Rotation of strong sphere disk 31 is normally coupled to the rotation of weak sphere disk 35. When the interlock key is depressed, the sphere directional keys move disk 31 while disk 35 remains stationary. A duction key, for simultaneous rotation of the Risley prisms of both refractor halves, is also included. For the auxiliary elements supported on disk 39 individual operation keys are provided. Set 537 includes a substantially identical set of keys. Key board 519 also includes a reset key and keys which control printer control board 521. In the event that microprocessor 527 is used not only to control both refractor halves but also a compact refraction instrument, such as disclosed in U.S. Pat. No. 4,395,097, key board 519 will also include a set of target and mode keys 539 and additional reset keys.

In response to a key being depressed, a circuit in key board 519 is closed and an electrical signal is sent to key board decoder 541 which, via a demultiplexer that senses which circuit was closed in key board 519, sends a code to microprocessor 527. There is a different code for each key and for each code there is an instruction in memory 529, which instruction results in signals being sent to motor driver board 511 to rotate one or more motors a predetermined number of steps in a particular direction. Microprocessor 527 also outputs new data to display 533 to indicate that the instruction has been carried out.

In order to hold disks 31–39, rotatable lens mounts such as illustrated at 53, and Risley prisms 353 and 355 in any given required position, all the motors are constantly energized at, approximately, ¼ power in order to maintain the magnetic detent and, thus, keep the motors from rotating. While the motors could be energized at full power, the lower power is preferred in order to reduce the size of the power supply required and to reduce heat dissipation. With this arrangement, motor driver board 511 includes, for each motor, a power up logic and a motor driver. With reference to FIG. 9, these are collectively designated 543 and 545.

In the preferred embodiment, the signals from microprocessor 527 to rotate, for instance, motor 243 a number of steps in a given direction are sent to both its motor driver and its power up logic. The motor driver keeps track of which two phases of motor 243 are on and which two phases are off. In response to the signals from microprocessor 527 to rotate shaft 265 of motor 243, the motor driver sequentially change which phases are on and which are off until the desired rotation is achieved. The power up logic includes the switching circuitry required to apply full power to, in this case, motor 243.

Printer control board 521, printer driver board 523 and thermal printer 525 are for providing a printout of: (1) the retinoscopy finding; (2) the distance prescription; (3) the near prescription; and (4) the complete prescription of the patient whose eyes are being examined. For this purpose, printer control board 521 has its own microprocessor 547, preferably an Intel 8039, and its own read only memory 549, preferably an Intel 8355 or 8755. Microprocessor 547 monitors the information sent to LED display 533 to determine if one of the print keys has been depressed. If a print key has been depressed, microprocessor 547 sends a signal to microprocessor 527 to send the requested refraction data to microprocessor 547 for printing. Printer control board 521 also includes an RS-232-C input/output port that can be used to input key codes from and output display data to a computer.

To rotate disk 31 from a position in which one strong sphere lens or opening is aligned with optical axis 61 to an immediately adjacent position where another lens or opening is aligned with axis 61 requires 18 steps of motor 243. As the gearing and motors are identical, 18 steps are also required to rotate each of disks 33–39 from one alignment position to an immediately adjacent alignment position. Further, because of the gear reduction, each step of motor 309 produces a one degree rotation of lens mounts 53, 57 and 59. Finally, each step of motors 413 and 423 rotates, respectively, prisms 353 and 355 one degree.

In order for microprocessor 527 to, for instance, rotate disk 31 from a position where one lens or opening is aligned with axis 61 to a position where another lens is aligned with axis 61, it is necessary to provide disk 31 with a reset or zero position from which all steps of motor 243 are counted. This is accomplished by encoder system 515 and reflective blocks. With reference to FIG. 1, disk 31 is provided with a reflective block 551 which cooperates with encoder 553, preferably a Texas Instruments TIL-139 or equivalent, positioned on comb assembly 73. Each of disks 33–39 is provided with an identical reflective block (not shown). Further, as is evident from inspection of FIG. 4, comb assembly 73 also includes optical encoders 555 and 557, for monitoring the positions of disks 35 and 39. For monitoring the positions of disks 33 and 37, comb assembly 75 is provided with two encoders, one of which is illustrated at 559 in FIG. 1.

Encoder 553, like all the encoders utilized, includes an LED and a phototransistor. Each phototransistor is coupled, and always sending an analog signal, to a separate terminal in OD encoder board 561. Board 561 also includes decoder logic which transforms these analog signals to digital signals, which are sent to interrupt decode logic system 531. For each encoder there is a separate terminal in logic 531. In operation, when the light emitted by the LED of encoder 553 is reflected back to the phototransistor by the leading edge of block 551 as it moves past encoder 553, the analog signal sent by encoder 553 changes. When the analog signal sent to board 561 reaches a threshold value, the decoder logic changes the digital signal sent to logic 531. For each motor, logic 531 includes a latch, preferably a J-K master slave flip-flop, which latches the rising edge of the change in signal from the decoder logic of board 561. In response to the latch being triggered, logic 531 sends an interrupt signal to microprocessor 527 that one of the latches has been triggered, and a signal to memory 529 which identifies which latch was triggered. If the rotation which triggered, for instance, encoder 553 was in response to a reset command from key board 519, microprocessor 527 reads interrupt data latched on memory 529 to find out which motor is associated with the interrupt signal received, and stops sending electrical pulses to, in the case of disk 31, motor 243. If the encoder is triggered in response to an instruction other than a reset instruction, the signal transmitted from logic 531 to microprocessor 527 is ignored.

Since, for instance, stepping motor 243 is programmed to index only in integral steps, it may be necessary, with motor 243 energized to hold it in one of its magnetic detent positions, to rotate motor support bracket 241 to insure proper alignment of the lenses supported on disk 31 with optical axis 61. To maintain this alignment, the electrical pulses which drive motor 243 must be interrupted so that motor 243 stops at that detent position where, in the case of disk 31, plano lens 60 is aligned with axis 61. Misalignment occurs if motor 243 stops rotating one step too soon or too late. This is true for disks 33–39. For the rotatable lens mounts and Risley prism 353 and 355, failure of the associated motor to stop at the correct detent position results in angular misorientation.

As those skilled in the art will appreciate, for motor 243 to stop at the correct detent position, encoder 553 must be triggered prior to the correct detent position but subsequent to the immediately preceeding detent position. Thus, the digital signal from encoder board 561 must be between two magnetic detent positions of motor 243 in order for microprocessor 527 to stop motor 243 at the step at which disk 31 is at its reset position. In view of manufacturing tolerances, it is necessary to be able to laterally adjust the position of each encoder to insure that the required signal is transmitted with the desired ½ step. With reference to FIG. 4, encoders 553, 555 and 557 are supported between forks 215 and 217 of comb assembly 73 on encoder support brackets 565, 567 and 569. Bracket 565 is secured to forks 215 and 217 via screws 571 and 573 which pass through slots 575 and 577 provided in tabs 579 and 581. Slots 575 and 577 permit the necessary lateral adjustment of encoder 553. Brackets 567 and 569 are identical in construction to, and adjusted in the same manner as bracket 565.

For Risley prisms 353 and 355 and the rotatable lens mounts, such as 53 and 57 which support the strong and weak cylinder lenses, pairs of encoders are required to insure that the associated motors stop precisely at the reset or starting position. With reference to the rotatable lens mounts, axis drive gear 303 is provided with 5 reflective blocks (not shown) equally angularly spaced about its periphery. Gear 341 is provided with reflective block 583. One encoder (not shown) is associated with gear 303; encoder 585, supported on post 587, with gear 341. With this arrangement, only when the phototransistors of both encoders are simultaneously above threshold and the resultant signals ANDed does encoder board 561 send the required digital signal to interrupt logic system 531. With the gear ratios and with 5 blocks on gear 303, this occurs for every 720 degree rotation of lens mounts 53, 57 and 59.

The encoder system for Risley prisms 353 and 355, illustrated in FIGS. 6 and 7, includes reflective blocks 591, 593, 595 and 597 and 4 encoders, three of which are illustrated at 601, 603 and 605. Encoders 601 and 605 are supported on adjustable brackets 607 and 609. With reference to, for instance, Risley prism 353, because mount 367 rotates only one degree for each step of motor 413, block 593 and encoder 603 cannot be positioned accurately enough to insure that encoder 603 will always be triggered prior to the correct detent position but subsequent to the immediately preceding detent position. In contrast to mount 367, gear 435 rotates three degrees for each step of motor 413 and, hence, block 591 and encoder 601 can be positioned to obtain the required accuracy. However, since gear 435 rotates 360 degrees for every 120 degree rotation of mount 367, encoder 601 cannot be used alone, but must be coupled with encoder 603. With this arrangement, only when the phototransistors of both encoders are simultaneously above threshold and the resultant signals ANDed, does encoder board 651 send the required digital signal to logic 531.

As is evident from inspection of FIG. 9, encoder system 515 also includes OS encoder board 611. Where microprocessor 527 is used not only to cohtrol both refractor halves but the compact refraction instrument disclosed in U.S. Pat. No. 4,395,097, an additional encoder board and set of encoders will be coupled to logic 531 and microprocessor 527.

Whereas the drawings and accompanying description have shown and described the preferred embodiment of the present invention, it should be apparent to those skilled in the art that various changes may be made in the form of the invention without affecting the scope thereof.

What we claim is:

1. In an ophthalmic instrument comprising: a base; a rotatable optical element; a stepping motor having a plurality of detent positions and a shaft for rotating said element; means, including a rotatable support for said element, for coupling said shaft to said element, whereby said motor can rotate said element relative to said base, one of the positions of said element wherein said motor is in one of said detent positions, constituting a reset or zero position; means for sending signals to said motor to rotate said element; and means for interrupting said signals to said motor before the magnetic detent position where said element is in said reset position but subsequent to the immediately preceding detent position, said means including at least two reflective blocks secured to said coupling means, a pair of encoders, decoder logic means for transforming analog signals to digital signals coupled to said encoders, and latch means coupled to both said decoder logic means and said means for sending signals to said motor, each of said encoders including an LED and a phototransistor, each of said phototransistors sending analog signals to said decoder logic means, which signals change when the light emitted by said corresponding LED is reflected back to said phototransistor by said corresponding block, said decoder logic means changing said digital signal when said analog signals from said encoders are concurrently above their threshold values and the resultant signals ANDed, said latch latching as a function of said change in digital signal and sending a signal to said means for sending signals to said monitor to stop sending signals to said motor.

2. The instrument as set forth in claim 1, wherein said support is a rotatable mount having gear teeth formed on the periphery thereof and said coupling means includes gear means, said gear and said mount having different rates of rotation, one being a multiple of the other.

3. The instrument as set forth in claim 2, wherein said element is a prism, one of said reflective blocks is positioned on said rotatable mount and the second of said reflective blocks is secured to said gear means, said gear means rotating 360 degrees for every 120 degree rotation of said support means.

4. The instrument as set forth in claim 2, wherein said element is a lens, said gear means includes first and second gears, said first gear having a plurality of reflective blocks evenly positioned about the periphery thereof, said second gear having a reflective block positioned thereon.

5. The instrument as set forth in claim 4, wherein said lens is a cylinder lens.

6. The instrument as set forth in claim 4, wherein said lens is a cross cylinder lens.

* * * * *